United States Patent
Dematio et al.

(10) Patent No.: US 9,173,806 B1
(45) Date of Patent: Nov. 3, 2015

(54) SYSTEMS AND METHODS FOR A STIMULATION DEVICE

(71) Applicants: Fnu Dematio, Singapore (SG); Kik Heong Gee, Singapore (SG)

(72) Inventors: Fnu Dematio, Singapore (SG); Kik Heong Gee, Singapore (SG)

(73) Assignee: Vibease Pte. Ltd., Singapore (SG)

( * ) Notice: Subject to any disclaimer, the term of this patent is extended or adjusted under 35 U.S.C. 154(b) by 0 days.

(21) Appl. No.: 14/483,881

(22) Filed: Sep. 11, 2014

(51) Int. Cl.
*A61H 1/00* (2006.01)
*A61H 23/00* (2006.01)

(52) U.S. Cl.
CPC ............ *A61H 23/00* (2013.01); *A61H 2201/50* (2013.01)

(58) Field of Classification Search
CPC ...................................................... A61H 23/00
USPC ............ 601/5, 23, 24, 26, 27, 33, 34, 35, 45, 601/49, 84, 86, 87, 89, 91, 93, 97, 98, 99, 601/101, 102, 107, 134, DIG. 23
See application file for complete search history.

(56) References Cited

U.S. PATENT DOCUMENTS

| | | | |
|---|---|---|---|
| 7,182,738 B2 * | 2/2007 | Bonutti et al. | 601/5 |
| 2007/0112284 A1 * | 5/2007 | Hoffman et al. | 601/46 |
| 2012/0253241 A1 * | 10/2012 | Levital et al. | 601/5 |

* cited by examiner

*Primary Examiner* — Quang D Thanh
(74) *Attorney, Agent, or Firm* — Pierson IP, PLLC

(57) ABSTRACT

Examples of the present disclosure are related to systems and methods for controlling stimulation movement on a stimulation device. Specifically, embodiments are related to changing a stimulation pattern on a stimulation device responsive to bio feedback data associated with a user.

16 Claims, 4 Drawing Sheets

SYSTEMS AND METHODS FOR A STIMULATION DEVICE

BACKGROUND INFORMATION

1. Field of the Disclosure

Examples of the present disclosure are related to systems and methods for controlling stimulation movement on a stimulation device. Specifically, embodiments are related to changing a stimulation pattern on a stimulation device responsive to bio feedback data associated with a user.

Stimulation movement consist one and of more movement but not limited such as vibration, stroke, thrust, tighten and rotation.

2. Background

Conventional stimulation devices are available for both men and women, and can be used with or without a partner. These stimulation devices can be strictly manual devices or can include stimulation mechanisms. The stimulation mechanisms in conventional stimulation devices are manually controlled by a user, wherein the user may interact with buttons on the stimulation device to control the frequency and/or amplitude of the stimulation movement.

However, a user may become distracted while performing actions to change the frequency and/or strength of the stimulation movement of the stimulation device.

Accordingly, needs exists for more efficient and effective systems and methods to operate and automate a stimulation device.

SUMMARY

Embodiments described herein disclose systems and methods wherein the stimulation movement may be dynamically modified, changed, and/or altered based on a user's or remote user's bio feedback.

Bio feedback is measured through sensors such as but not limited to heart rate, brain waves, blood pressure, body temperature, penis erection, vaginal lubrication, Kegel muscles pressure.

Embodiments described herein disclose systems and methods can be associated with synchronizing stimulation movement to content, wherein the stimulation movement may be dynamically modified, changed, and/or altered based on a user's bio feedback.

In embodiments, stimulation movement can be synchronized to segments of content, such as audio based content, video based content, multimedia based content, etc. As the user is interacting with, listening to, or viewing a segment of content, a synchronization trigger may be initiated, wherein the synchronization trigger may initiate a stimulation device to move, vibrate, rotate, stroke, thrust, pulsate, etc. in a first stimulation movement. The stimulation movement may include frequency and/or the strength of vibrations, thrusts, strokes and rotates. In embodiments, while the user is interacting with, viewing, or listening to the segment of content, a bio feedback sensor may monitor and record bio feedback data associated with the user. Responsive to a synchronization trigger being initiated, the stimulation movement of the stimulation device may be dynamically determined, changed, and/or altered based on the user's bio feedback data, In embodiments, the user's bio feedback data may be recorded by a plurality of sensors. For example, the user's heart rate may be determined by a heart rate monitor, the user's brain waves may be determined by an electroencephalography (EEG) device, or any other bio feedback sensors may determine other bio feedback measurements (referred to hereinafter individually and collectively as bio feedback data) associated with the user.

In embodiments, if a user's bio feedback data is greater than or equal to a bio feedback threshold, then the stimulation device may dynamically change from a first stimulation movement to a second stimulation pattern. In embodiments, if the user's bio feedback measurements increase at a rate greater than a rate threshold, then the stimulation device may dynamically change from the first stimulation movement to a second stimulation movement.

In embodiments, the first stimulation movement and/or second movement may be preset and/or set by a user before watching, listening to, and/or interacting with content. Furthermore, in embodiments, a user may dynamically alter, change, and/or modify the first stimulation movement utilizing an interface of the stimulation device to increase and/or decrease the stimulation device's amplitude, frequency, speed, strength, etc.

These, and other, aspects of the invention will be better appreciated and understood when considered in conjunction with the following description and the accompanying drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE DRAWINGS

Non-limiting and non-exhaustive embodiments of the present embodiments are described with reference to the following figures, wherein like reference numerals refer to like parts throughout the various views unless otherwise specified.

Figure 1:
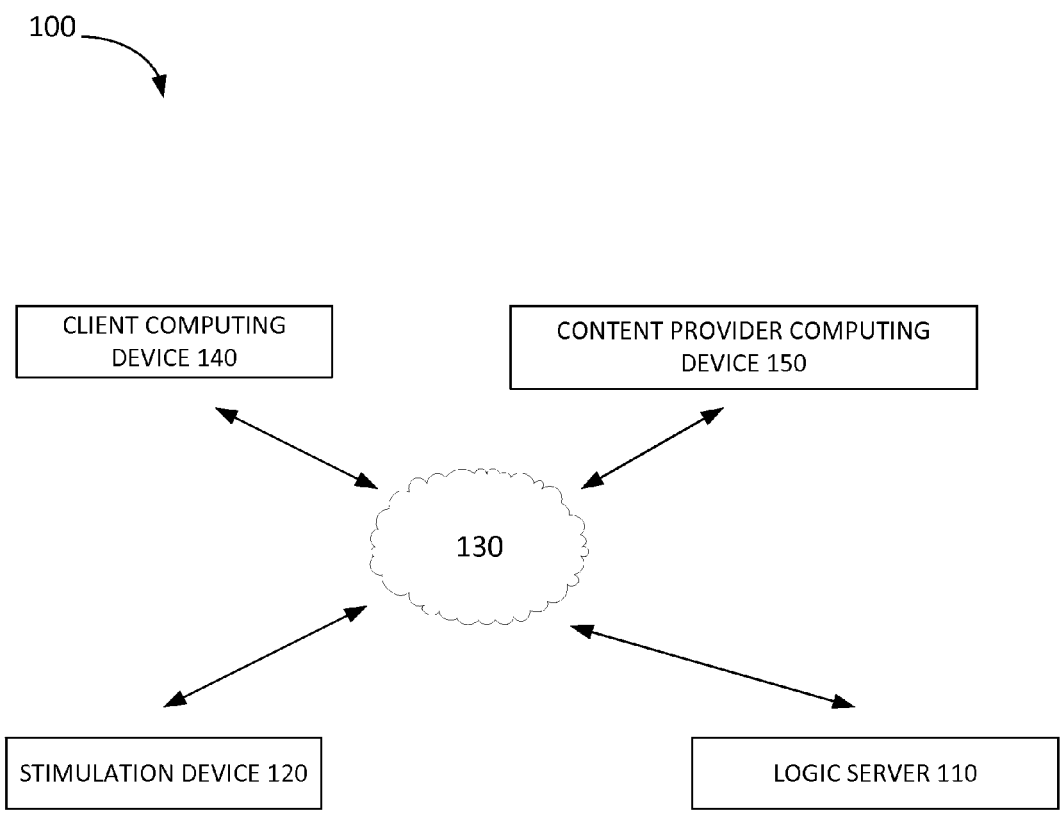
FIG. 1 depicts one embodiment of a topology to change stimulation movements based on a user's bio feedback data.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Embodiments described herein disclose systems and methods associated with synchronizing stimulation movements with segments of content, wherein the stimulation movements may be dynamically changed, modified and/or altered based on a user's bio feedback data.

Turning now to FIG. 1, FIG. 1 depicts one topology to change stimulation movements based on a user's bio feedback data. Topology 100 may include a logic server 110, stimulation device 120, client computing device 140, and content provider computing device 150. The elements depicted in topology 100 may be communicatively coupled to each other over network 130.

Network 130 may be a wired or wireless network such as the Internet, an intranet, a LAN, a WAN, a NFC network, Bluetooth, infrared, radio frequency, a cellular network, or another type of network. It will be understood that network 130 may be a combination of multiple different kinds of wired or wireless networks.

Logic server 110 may be a computing device, such as a general hardware platform server configured to support mobile applications, point of sale (POS) devices, software, and the like executed on stimulation device 120, client computing device 140, or content provider computing device 150. Logic server 110 may include physical computing devices residing at a particular location or may be deployed in a cloud computing network environment. In this description, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.). Logic server 110 may include any combination of one or more computer-usable or computer-readable media.

For example, logic server 110 may include a computer-readable medium including one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device.

In embodiments, logic server 110 may be configured to receive content from content provider computing device 150, transmit the content to client computing device 140, receive bio feedback data from client computing device 140, and transmit data to change stimulation movement to stimulation device 120.

Stimulation device 120 may be a device that is configured to stimulate nerves for a pleasurable feeling. Stimulation device 120 may be shaped and/or sized in various designs, wherein the designs may be configured to ergonomically stimulate erogenous zones for erotic stimulation. Stimulation device 120 may include vibration mechanism, rotating mechanism, thrusting mechanism, stroking mechanism, tightening mechanism, etc. Stimulation device 120 may change to various stimulation movements, wherein the stimulation movements may have different pulse rates, frequencies, amplitudes, duration, speed, strength etc. Stimulation device 120 may include a communication device configured to receive synchronization data from logic server 110 and/or client computing device 140. Responsive to stimulation device 120 receiving the synchronization data, stimulation device 120 may initiate a stimulation movement corresponding to the synchronization data. Stimulation device 120 may also be configured to determine bio feedback data, wherein the stimulation data may alter, change, or modify the stimulation movement corresponding to the synchronization data. In embodiments, stimulation device 120 may also include a user interface, such as buttons, to change the stimulation movement. For example, a user may press the buttons to change the pulse rate, frequency, amplitude, speed, strength, etc. associated with the stimulation movement.

Client computing device 140 may be a laptop computer, desktop computer, smart phone, tablet computer, personal data assistant, or any other type of device with a hardware processor that is configured to process instructions, connect to network 130, present content to a user, receive inputs from a user, determine bio feedback data for the user, transmit the bio feedback data to logic server 110, transmit stimulation movement data to stimulation device 120, and/or transmit synchronization data to stimulation device 120.

Content provider computing device 150 may be a hardware computing device that is configured to transmit content to logic server 110 and/or client computing device 140 via network 130. The transmitted content may be a text, audio, still images, animation, video, interactive content forms, etc., or any such combination, which may be configured to be presented to a user via client computing device 140. The content may include synchronization data that is embedded within the content, wherein the synchronization data may trigger stimulation device 120 to initiate a stimulation movement. The synchronization data may be determined to trigger the stimulation movement at various segments of content while the user is watching, listening to, or interacting with content. In embodiments, the synchronization data may include segment data and a stimulation movement, wherein different synchronization data may include different stimulation movements and may be associated with different segments of content. Therefore, while the user is being presented with content, different segments of the content may cause different stimulation movements via stimulation device 120.

One skilled in the art will appreciate that in different network topologies associated with embodiments, different system elements may transmit and/or receive different data. For example, in another network topology, content may be created by client computing device 140, and transmitted to logic server 110. Accordingly, the above network topology is a non-limiting example embodiment.

Figure 2:
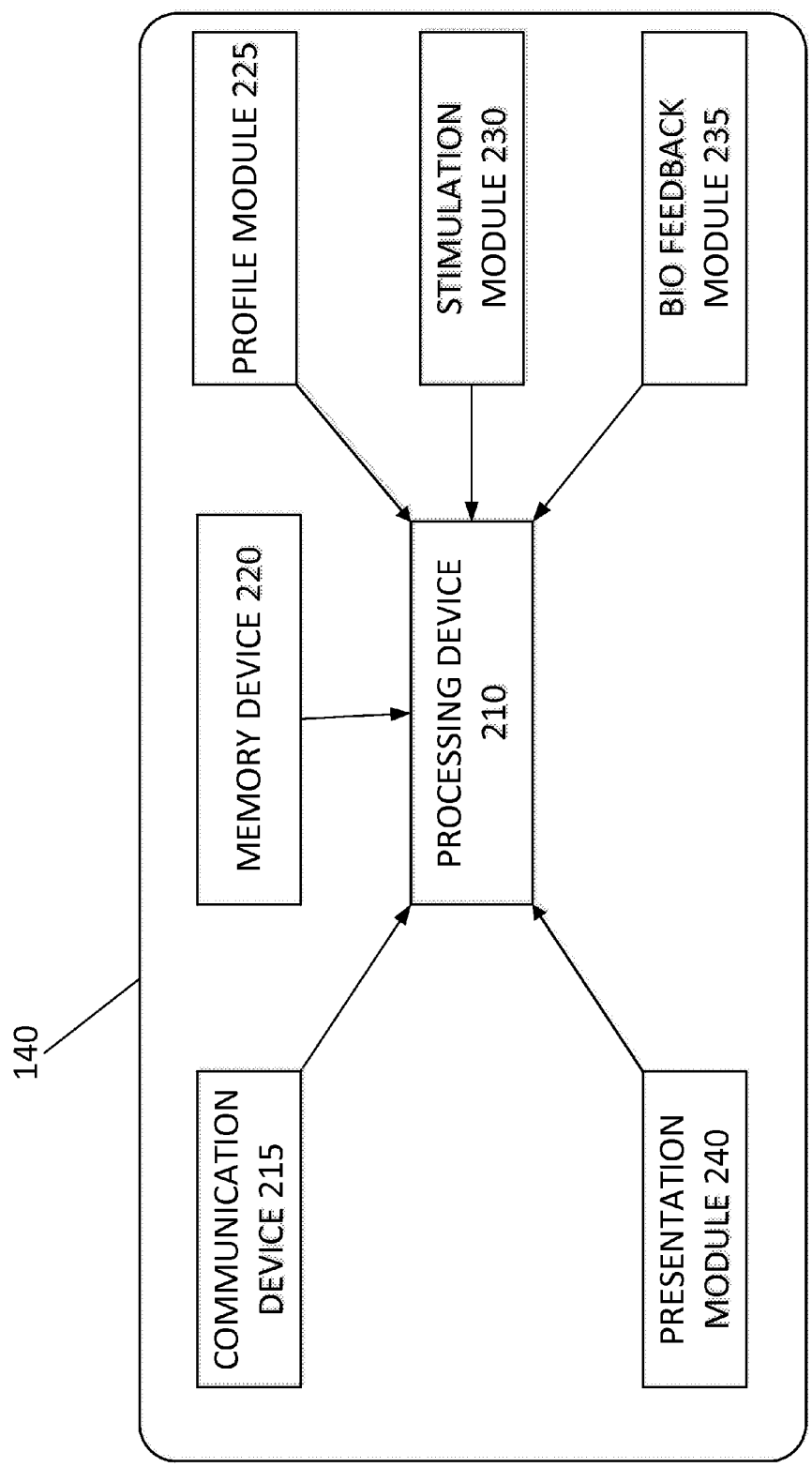
FIG. 2 depicts one embodiment of a client computing device.

FIG. 2 depicts one embodiment of client computing device 140. Client computing device 140 may include processing device 210, communication device 215, a memory device 220, a profile module 225, stimulation module 230, a bio feedback module 235, and a presentation module 240.

Processing device 210 can include memory, e.g., read only memory (ROM) and random access memory (RAM), storing processor-executable instructions and one or more processors that execute the processor-executable instructions. In embodiments where processing device 210 includes two or more processors, the processors may operate in a parallel or a distributed manner. Processing device 210 may execute an operating system of client computing device 140 or software associated with other elements of client computing device 140.

Communication device 215 may be a device that allows client computing device 140 to communicate with another device, e.g., a logic server or a content provider computing device over a network. Communication device 215 may include one or more wireless transceivers for performing wireless communication and/or one or more communication ports for performing wired communication.

Memory device 220 may be a device configured to store data generated or received by client computing device 140. Memory device 220 may include, but is not limited to a hard disc drive, an optical disc drive, and/or a flash memory drive. Memory device 220 may be configured to store content, synchronization data associated with content, a profile associated with a user, bio feedback data associated with the user, stimulation movement data, etc.

Profile module 225 may be a hardware processing device configured to allow the user of a client computing device 140 to generate and create a user profile. The user's profile may include information stored in memory device 220 and/or other storage locations. The user's profile may include user information and bio feedback data. The user information may include, for example, information identifying users (e.g., a username or handle, a number, an identifier, and/or other identifying information), security login information (e.g., a login code or password), payment information (e.g., credit card information), etc. The bio feedback data may include bio feedback data associated with the user determined by bio feedback module 235. In embodiments, the bio feedback data may include baseline values associated with a user's heart rate, brain wave activity, blood pressure, body temperature, penis erection, vaginal lubrication, etc. The baseline bio feedback data may be utilized to determine if there is a change in bio feedback data greater than or lesser than a bio feedback threshold.

Stimulation module 230 may be a hardware processing device configured to allow a user to set synchronization data associated with content, wherein the synchronization data may include a time associated with a segment of content to initiate a stimulation movement, a desired stimulation movement, and a bio feedback threshold associated with the synchronization data. In embodiments, a user may utilize stimulation module 230 to modify, change, and/or alter synchronization data associated with content received from content provider computing device 150. Utilizing stimulation module 230, a user may create synchronization data that initiates a desired stimulation movement implemented by stimulation device 120 when a certain segment of content is being presented. Therefore, as the user is viewing, listening to, and/or interacting with the segment of content, stimulation device 120 may begin to move at a desired stimulation movement, wherein the segment of content may have a start period and/or an end period in which the stimulation movement is ongoing. In embodiments, the user may also set bio feedback thresholds, wherein if the user's bio feedback data changes at a rate greater than a bio feedback threshold or is greater than or equal to a bio feedback threshold, then the stimulation movement currently implemented on stimulation device 120 may be modified to increase and/or decrease in frequency, amplitude, speed, strength, etc., and/or a new stimulation movement may be implemented.

Bio feedback module 235 may be a hardware processing device configured to determine a user's bio feedback data. For example, bio feedback module 235 may be configured to determine a user's heart rate, electroencephalography (EEG) data, or any other form of quantifiable data associated with user characteristics and/or traits. Bio feedback module 235 may be configured to continuously determine a user's bio feedback data, determine a user's bio feedback data at set intervals, determine bio feedback during a segment of content, and/or determine a user's bio feedback responsive to the user performing actions associated with stimulation device 120 and/or client computing device 140. For example, bio feedback module 235 may include a microprocessor that is configured to continuously monitor a user's heart over a period of time, such as an electrocardiography device. In embodiments, bio feedback module 235 may quantify a user's heart beat in beats per second, minute, or any other desired time period. Bio feedback module 235 may also include an EEG device configured to record a user's EEG data by recording the electrical activity along a user's scalp. The EEG device may measure voltage fluctuations resulting from ionic currents flowing within the neurons of the user's brain. Responsive to determining the user's bio feedback data, bio feedback module 235 may transmit the determined bio feedback data to logic server 110 and/or store the bio feedback data within memory device 220. Bio feedback module 235 may also include a moisture sensor to detect the vagina lubrication.

Presentation module 240 may be a hardware processing that may receive information configured to be presented to a user. Presentation module 240 may include a user interface, wherein the term "user interface" may include, but is not limited to being, a monitor, a speaker, a touch screen, a physical keyboard, a mouse, a camera, a video camera, a microphone, etc. Presentation module 240 may be configured to present content to the user, such as multimedia via a speaker and/or monitor. Furthermore, presentation module 240 may be configured to allow a user to control the stimulation movements of stimulation device 120, set baseline values associated with a user's bio feedback data, set bio feedback thresholds associated with a user's bio feedback data, and/or set synchronization data associated with stimulation movements initiated at various segments of content.

Figure 3:
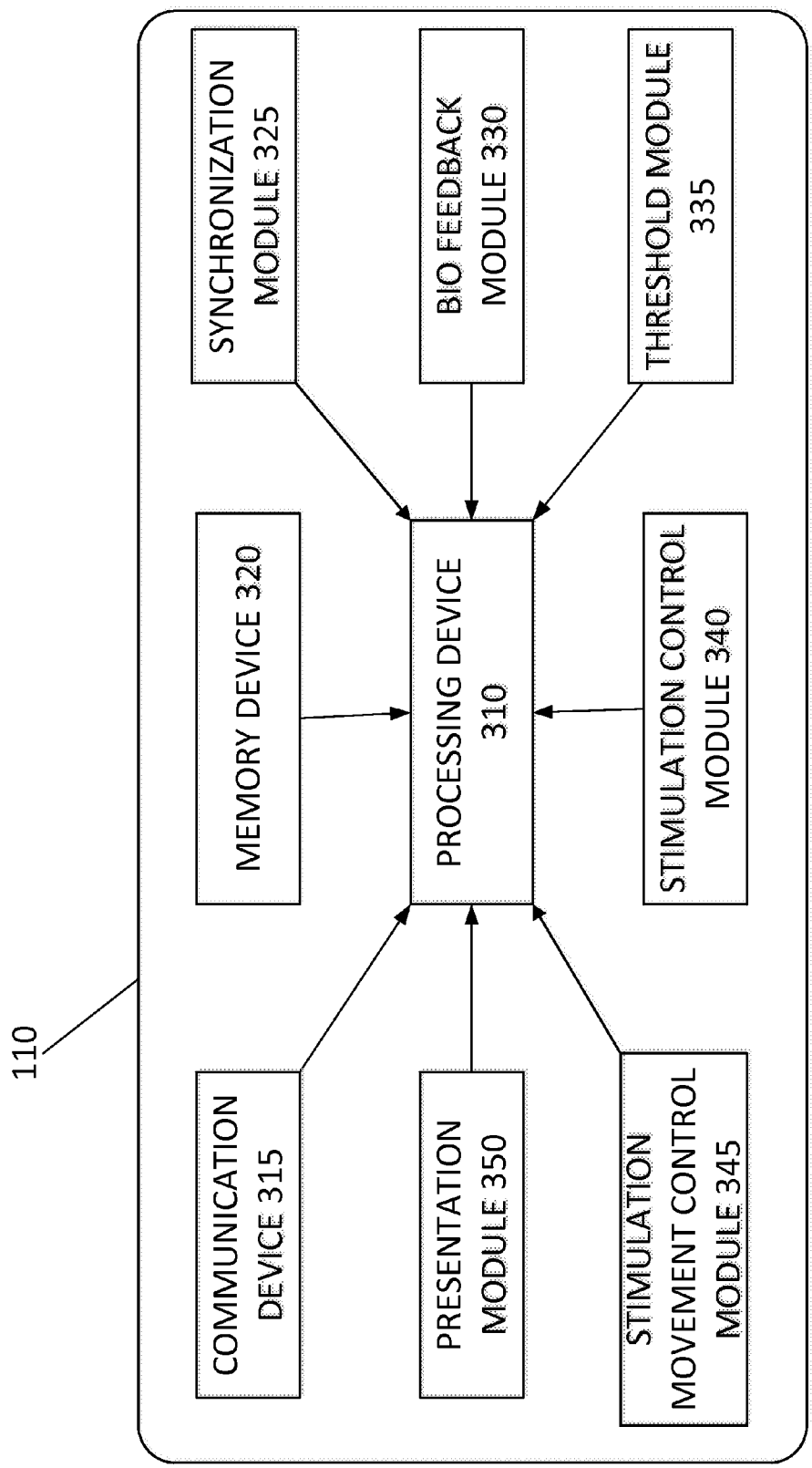
FIG. 3 depicts one embodiment of a logic server.

FIG. 3 depicts one embodiment of logic server 110. One skilled in the art will appreciate that other network elements in a topology, such as a client computing device may perform the similar and/or the same processes as described below. Logic server 110 may include processing device 310, communication device 315, memory device 320, a synchronization module 325, a bio feedback module 330, a threshold module 335, a stimulation movement module 345, a stimulation control module 340, and a presentation module 350.

Processing device 310 can include memory, e.g., read only memory (ROM) and random access memory (RAM), storing processor-executable instructions and one or more processors that execute the processor-executable instructions. In embodiments where processing device 310 includes two or more processors, the processors may operate in a parallel or a distributed manner. Processing device 310 may execute an operating system of logic server 110 or software associated with other elements of logic server 110.

Communication device 315 may be a device that allows logic server 110 to communicate with another device, e.g., a stimulation device, client computing device, or a content provider computing device over a network. Communication device 315 may include one or more wireless transceivers for performing wireless communication and/or one or more communication ports for performing wired communication.

Memory device 320 may be a device configured to store data generated or received by logic server. Memory device 320 may include, but is not limited to a hard disc drive, an optical disc drive, and/or a flash memory drive. In embodiments, memory device 320 may be configured to store content received from content provider computing device 150, bio feedback data received from client computing device 140, synchronization data, stimulation movements, etc.

Synchronization module 325 may be a hardware processing device configured to synchronize data to initiate stimulation movements with segments of content. Synchronization module 325 may utilize synchronization data received from client computing device 140 and/or content provider computing device 150, wherein the synchronization data may include a time associated with the content to initiate a stimulation movement, a desired stimulation movement, and bio feedback thresholds associated with bio feedback data. In embodiments, when a user is viewing, listening to, and/or interacting with a segment of content (e.g. a time marker, scene, song, etc.), synchronization module 325 may be configured to transmit a stimulation movement to stimulation device 120. Responsive to stimulation device 120 receiving the synchronization data, stimulation device 120 may initiate a stimulation movement identified in the synchronization data.

Bio feedback module 330 may be a hardware processing device configured to receive bio feedback data from client computing device 140 and/or stimulation device 120, and store the bio feedback data in memory device 320. The received bio feedback data may be associated with any bio feedback measurement associated with a user, and may be received continuously and/or at set intervals. In embodiments, the bio feedback data may include baseline data, which may be recorded before a user is interacting with content.

Threshold module 335 may be a hardware processing device configured to determine bio feedback thresholds and ranges. The thresholds and/or ranges may indicate that a user's bio feedback data has increased and/or decreased past a certain metric. For example, threshold module 335 may include a set threshold, wherein the set threshold is a certain number of beats per minute and/or a certain number of beats per minute above or below the user's baseline heart rate. Furthermore, threshold module 335 may include a change threshold, wherein the change threshold may indicate that the user's heartbeat has increased above a certain number of beats per minute, which may be independent of the user's baseline bio feedback. In other embodiments, the set thresholds and/or change thresholds may be associated with other bio feedback data, such as EEG metrics. The threshold ranges or change threshold may be associated the user's mood while watching, listening to, and/or interacting with content. For example, if a user's bio feedback data increases past a bio feedback threshold while listening to, watching, and/or interacting with content, it may indicate that the user is aroused by a certain segment of content.

Stimulation movement module 345 may be a hardware processing device configured to store stimulation movements. The stimulation movements may be associated with how stimulation device 120 should move, wherein the stimulation movements may have different type of movement, pulse rates, frequencies, amplitudes, speed, strength etc. For example, a first stimulation movement may include a movement type, first amplitude and a first frequency and a second stimulation movement may have a second movement type, second amplitude and a second frequency, wherein the first and second amplitudes and frequencies are different values. In embodiments, the second stimulation movement may be a value that change the type of movement from vibrating to rotating, thrusting to vibrating. The stimulation movement currently implemented on the stimulation device 120 (e.g. the first stimulation movement) at a set value. For example, the second stimulation movement may be rotating at double the frequency currently implemented by the stimulation device 120.

Stimulation movement control module 345 may be a hardware processing device configured to initiate, modify, change, and/or alter a stimulation movement on stimulation device 120 based on the user's bio feedback data. Stimulation movement control module 345 may be configured to initiate and/or stop a first stimulation movement on stimulation device 120 responsive to the synchronization data, wherein the synchronization data may indicate the segment to start and/or stop the first stimulation movement. While watching, listening to, and or interacting with a segment of content, the user may alter, modify, and/or set the first stimulation movement.

Furthermore, stimulation movement module 345 may compare received bio feedback data from the user with thresholds to determine if the received bio feedback data is greater than or lesser than or equal to a bio feedback threshold. Responsive to stimulation control module 345 determining that the received bio feedback data is greater than a bio feedback threshold, stimulation movement module 345 may be configured to transmit change data to stimulation device 120, to change stimulation device 120 from a first stimulation movement to a second stimulation movement during a segment of content. For example, if a user is listening to, viewing, and/or interacting with a segment of content with synchronization data indicates stimulation device 120 should be vibrating at a first stimulation movement and stimulation movement module 345 determines that a user's heart rate is greater than a heart rate threshold, then stimulation control module 345 may be configured to transmit change data to stimulation device 120 to change from the first stimulation movement to a second stimulation movement during the segment and/or until the user's bio feedback data (e.g. heart rate) falls below the bio feedback threshold.

Presentation module 350 may be a hardware processing that may receive information configured to be presented to a user of logic server 110. Presentation module 345 may include a user interface, wherein the term "user interface" may include, but is not limited to being, a monitor, a speaker, a touch screen, a physical keyboard, a mouse, a camera, a video camera, a microphone, etc. Presentation module 345 may be configured to allow a user to set synchronization data associated with stimulation movements and/or segments of content (e.g. when a stimulation movement should be initiated on stimulation device 120, set bio feedback baseline values, threshold values, etc.

Figure 4:
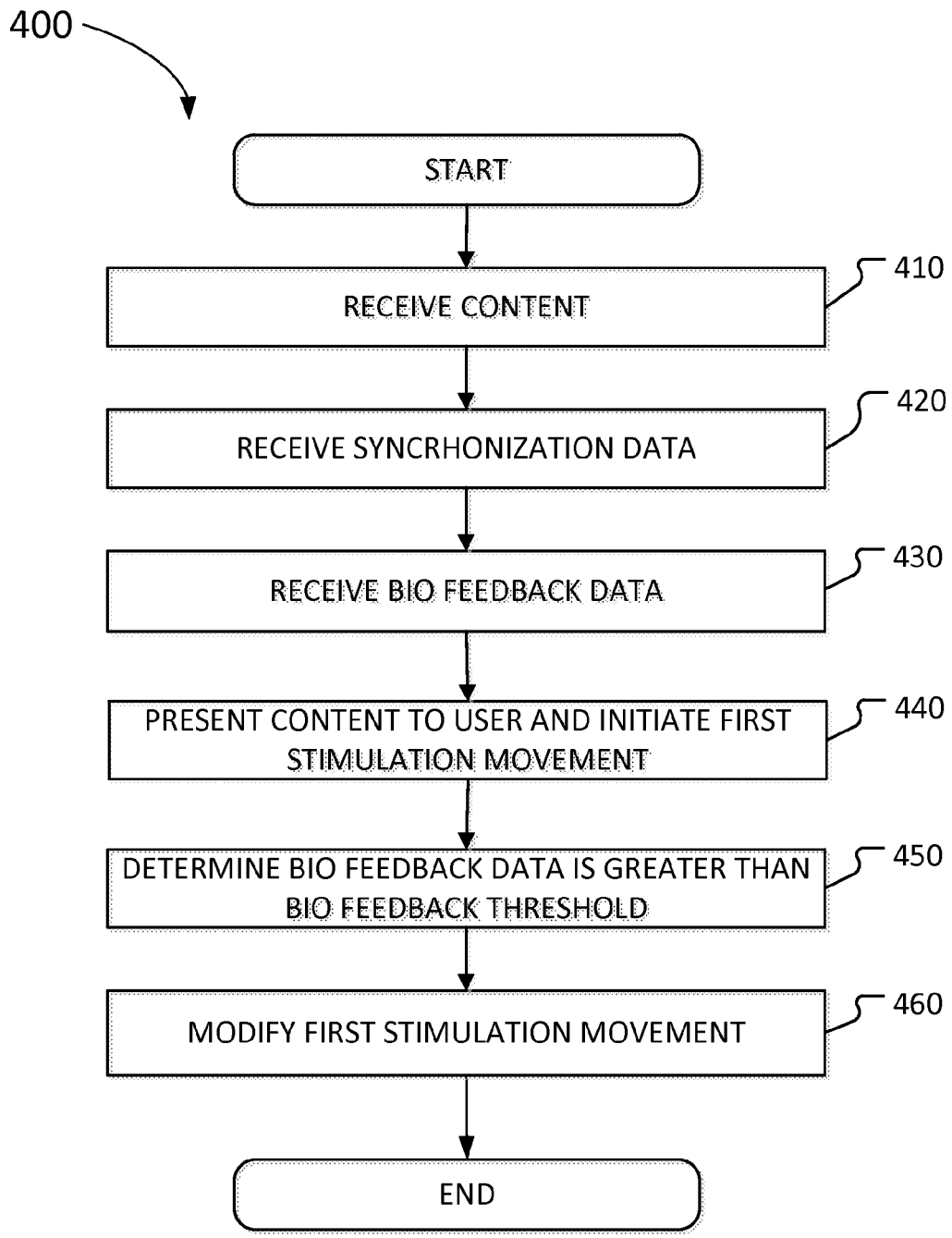
FIG. 4 depicts one method of a method for modifying stimulation movements on a stimulation device based on a user's bio feedback data.

FIG. 4 illustrates a method 400 for modifying stimulation movements on a stimulation device based on a user's bio feedback data. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At operation 410, content may be received. The content may be received from a content provider computing device and/or a client computing device. The received content may be any form of media that a user may view, listen to, and/or interact with. For example, the content may be a movie, audio book, interactive game, etc. Operation 410 may be performed by a synchronization module that is the same as or similar to synchronization module 325, in accordance with one or more implementations.

At operation 420, synchronization data may be received. Responsive to a segment of the received content being presented to a user, the synchronization data may initiate a first stimulation movement on a stimulation device. Therefore, while the user is listening to, watching, and/or interacting with a segment of content, the first stimulation movement may be automatically initiated on the stimulation device without receiving any input from the user. The synchronization data may be set by a user of a client computing device, content provider computing device, and/or a user of a logic server. Furthermore, a user of a client computing device may determine what stimulation movements should be initiated at various segments of content after receiving the content from a content provider computing device, and/or a user of a content provider computing device may preset the stimulation movements associated with various segments of the content before transmitting the content to the logic server and/or client computing device. Operation 420 may be performed by a synchronization module that is the same as or similar to synchronization module 325, in accordance with one or more implementations.

At operation 430, bio feedback data from a user may be received. The received bio feedback data may be associated with any bio feedback associated with a user. For example, the received bio feedback data may be associated with a user's heart rate, EEG measurements, etc. The received bio feedback data may be received at set intervals and/or continuously. Operation 430 may be performed by a bio feedback module that is the same as or similar to bio feedback module 325, in accordance with one or more implementations.

At operation 440, a first stimulation movement may be initiated on a stimulation device responsive to a first segment of content being presented to a user. The first stimulation movement may cause the stimulation device to vibrate, pulsate, etc. at a first frequency, first amplitude, etc. Operation 440 may be performed by a stimulation movement module that is the same as or similar to stimulation movement module 335, in accordance with one or more implementations.

At operation 450, it may be determined that the user's bio feedback data is greater than a bio feedback threshold while watching, listening to, and/or interacting with the segment of content. For example, it may be determined that the user's heart rate is greater than a certain beats per minute and/or the user's heart rate has increased a certain beats per minute over a time period. Operation 450 may be performed by a stimulation control module that is the same as or similar to stimulation control module 340, in accordance with one or more implementations.

At operation 460, responsive to determining that the user's bio feedback data is greater than the bio feedback threshold watching, listening to, and/or interacting with the segment of content, data indicating that the first stimulation movement and/or the stimulation movement implemented on the stimulation device should be modified, altered, and/or changed to a second vibration. For example, the second stimulation movement may cause the first stimulation movement and/or the stimulation movement implanted on the stimulation device to increase in frequency, amplitude, etc. Operation 460 may be performed by a stimulation control module that is the same as or similar to stimulation control module 340, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

Reference throughout this specification to "one embodiment", "an embodiment", "one example" or "an example" means that a particular feature, structure or characteristic described in connection with the embodiment or example is included in at least one embodiment of the present invention. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

Embodiments in accordance with the present invention may be embodied as an apparatus, method, or computer program product. Accordingly, the present embodiments may take the form of an entirely hardware embodiment, an entirely software embodiment (including firmware, resident software, micro-code, etc.), or an embodiment combining software and hardware aspects that may all generally be referred to herein as a "module" or "system." Furthermore, the present invention may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present invention may be written in any combination of one or more programming languages.

The flowcharts and block diagrams in the flow diagrams illustrate the architecture, functionality, and operation of possible implementations of systems, methods, and computer program products according to various embodiments of the present invention. In this regard, each block in the flowcharts or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowcharts and/or block diagrams.

Embodiments described herein disclose systems and methods associated with synchronizing vibrations to content, wherein the vibrations may be dynamically modified based on a user's bio feedback.

What is claimed is:

1. A system to control a hardware stimulation device, the system comprising:
   a bio feedback processing device configured to receive bio feedback data;
   a stimulation control processing device configured to determine that the bio feedback data is greater than or equal to a bio feedback threshold, the stimulation control processing device configured to transmit data to change a stimulation movement implemented on the hardware stimulation device responsive to the bio feedback data being greater than or equal to the bio feedback threshold, the biofeedback threshold being associated with a first segment of content, the first segment of content including a time marker with a start period and an end period, the first segment of content being multimedia content;
   a synchronization processing device configured to transmit synchronization data to initiate a first stimulation movement on the hardware stimulation device responsive to the first segment of content being presented to a user, wherein the stimulation control processing device is configured to transmit change data to change the first stimulation movement to a second stimulation movement responsive to determining that the bio feedback data is greater than or equal to the bio feedback threshold associated with the first segment of content during the first segment of content.

2. The system of claim 1, wherein the stimulation movement includes a stimulation movement type, frequency, amplitude, duration, speed and strength.

3. The system of claim 2, wherein the synchronization data is set by at least one of the user being present with the content and an administrator of a content provider computing device transmitting the content to a communication device.

4. The system of claim 2, wherein the first or the second stimulation movement includes at least one of vibration, rotation and thrusting.

5. The system of claim 1, wherein the second stimulation movement is independent of the first stimulation movement, the second stimulation movement including at least one of a second movement type, a second frequency, a second amplitude, a second duration and a second strength.

6. The system of claim 1, wherein the second stimulation movement changes a stimulation movement type from rotation to vibration, a first vibration frequency, or a first vibration amplitude by a fixed amount.

7. The system of claim 1, wherein the bio feedback data is associated with at least one of a heart rate, brain waves, blood pressure, body temperature, penis erection, vaginal lubrication, or Kegel muscles pressure.

8. The system of claim 7, wherein the bio feedback threshold is associated with a change in the heart rate of a user, the bio feedback threshold being associated with at least one of an increase in beats per minute from a baseline heart rate of the user and a set beats per minute.

9. The system of claim 1, wherein the content includes at least one of audio content, video content, or text based content.

10. A method to control a hardware stimulation device, the method comprising:
    receiving bio feedback data;
    determining that the bio feedback data is greater than or equal to a bio feedback threshold, the bio feedback threshold being associated with a first segment of content, the first segment of content including a time marker with a start period and an end period, the first segment of content being multimedia content;
    initiating a first stimulation movement on the hardware stimulation device responsive to presenting the first segment of content is to a user;
    transmitting change data to change the first stimulation movement to a second stimulation movement responsive to determining that the bio feedback data is greater than or equal to the bio feedback threshold associated with the first segment of content during the first segment of content.

11. The method of claim 10, wherein the first stimulation movement includes a movement type, frequency, amplitude, speed, strength, or duration.

12. The method of claim 11, wherein the synchronization data is set by at least one of a user being presented with the content or an administrator of a content provider computing device transmitting the content.

13. The method of claim 10, wherein the second stimulation movement is independent of the first stimulation movement, the second stimulation movement including a second movement type, a second frequency, a second amplitude, a second duration, and a second strength.

14. The method of claim 13, wherein the second stimulation movement changes a stimulation movement type from rotation to vibration, a first vibration frequency, or a first vibration amplitude by a fixed amount.

15. The method of claim 10, wherein the bio feedback data is associated with at least one of a heart rate, brain waves, blood pressure, body temperature, penis erection, vaginal lubrication or Kegel muscles pressure.

16. The method of claim 15, wherein the bio feedback threshold is associated with a change in one of more bio feedback data, the bio feed threshold being associated with at least one of an increase in beats per minute from a baseline heart rate of a user and a set beats per minute.

* * * * *